United States Patent [19]

Greene et al.

[11] 4,352,212
[45] Oct. 5, 1982

[54] JOINT PROSTHESIS

[75] Inventors: David J. Greene, Boston, Mass.;
Peter S. Walker, Ridgewood, N.J.

[73] Assignee: Howmedica, Inc., New York, N.Y.

[21] Appl. No.: 161,503

[22] Filed: Jun. 20, 1980

Related U.S. Application Data

[63] Continuation of Ser. No. 17,486, Mar. 5, 1979, abandoned.

[51] Int. Cl.³ .............................................. A61F 1/03
[52] U.S. Cl. .................................... 3/1.91; 128/92 C
[58] Field of Search ................... 3/1.911, 1.912, 1.913, 3/1.91; 128/92 C

[56] References Cited

U.S. PATENT DOCUMENTS

| | | |
|---|---|---|
| 2,785,673 | 3/1957 | Anderson . |
| 3,462,765 | 8/1969 | Swanson . |
| 3,506,982 | 4/1970 | Steffee ......................... 128/92 C X |
| 3,593,342 | 7/1971 | Niebauer . |
| 3,868,730 | 3/1975 | Kaufer et al. ........................... 3/1.91 |
| 3,869,729 | 3/1975 | Attenborough ............. 128/92 C X |
| 3,990,118 | 11/1976 | Strickland et al. ........... 128/92 C X |
| 3,991,425 | 11/1976 | Martin et al. ............................ 3/1.91 |
| 3,992,726 | 11/1976 | Freeman et al. ........................ 3/1.91 |
| 4,011,603 | 3/1977 | Steffee .................................... 3/1.91 |
| 4,059,854 | 11/1977 | Laure ...................................... 3/1.91 |
| 4,063,314 | 12/1977 | Loda ....................................... 3/1.91 |
| 4,112,522 | 9/1978 | Dadurian et al. ................. 3/1.911 X |
| 4,136,405 | 1/1979 | Pastrick et al. ....................... 3/1.911 |
| 4,156,296 | 5/1979 | Johnson et al. ........................ 3/1.91 |
| 4,158,893 | 6/1979 | Swanson ................................. 3/1.91 |
| 4,183,104 | 1/1980 | Frey ....................................... 3/1.91 |
| 4,194,250 | 3/1980 | Walker ................................... 3/1.91 |
| 4,219,893 | 9/1980 | Noiles ................................... 3/1.911 |

FOREIGN PATENT DOCUMENTS

| | | |
|---|---|---|
| 1153449 | 5/1969 | United Kingdom . |
| 1413477 | 11/1975 | United Kingdom . |
| 1443470 | 7/1976 | United Kingdom . |
| 1461154 | 1/1977 | United Kingdom . |
| 1493213 | 11/1977 | United Kingdom . |
| 1507309 | 4/1978 | United Kingdom . |
| 1514479 | 6/1978 | United Kingdom . |
| 2015882 | 9/1979 | United Kingdom . |
| 1553836 | 10/1979 | United Kingdom . |
| 1554956 | 10/1979 | United Kingdom . |

*Primary Examiner*—Clifford D. Crowder
*Attorney, Agent, or Firm*—Pennie & Edmonds

[57] ABSTRACT

A novel joint prosthesis, particularly suitable as a metacarpophalangeal joint prosthesis, is disclosed comprising first and second intramedullary plugs adapted to be secured to the walls of the intramedullary canals of the two bones forming the joint, and first and second components each comprising a bearing portion and a stem slidably received in a longitudinal bore provided in each of said intramedullary plugs. Transmission of stresses to the bone-prosthesis fixation interfaces is substantially reduced as a result of the freedom of motion of the stems within these longitudinal bores. In a preferred embodiment, axial rotation of one, but only one, of said stems with respect to the intramedullary plug receiving it is prevented. Use of preferred configurations for the bearing portions of the two components provides an accurate reproduction of the movement and degrees of freedom of the natural metacarpophalangeal joint.

31 Claims, 10 Drawing Figures

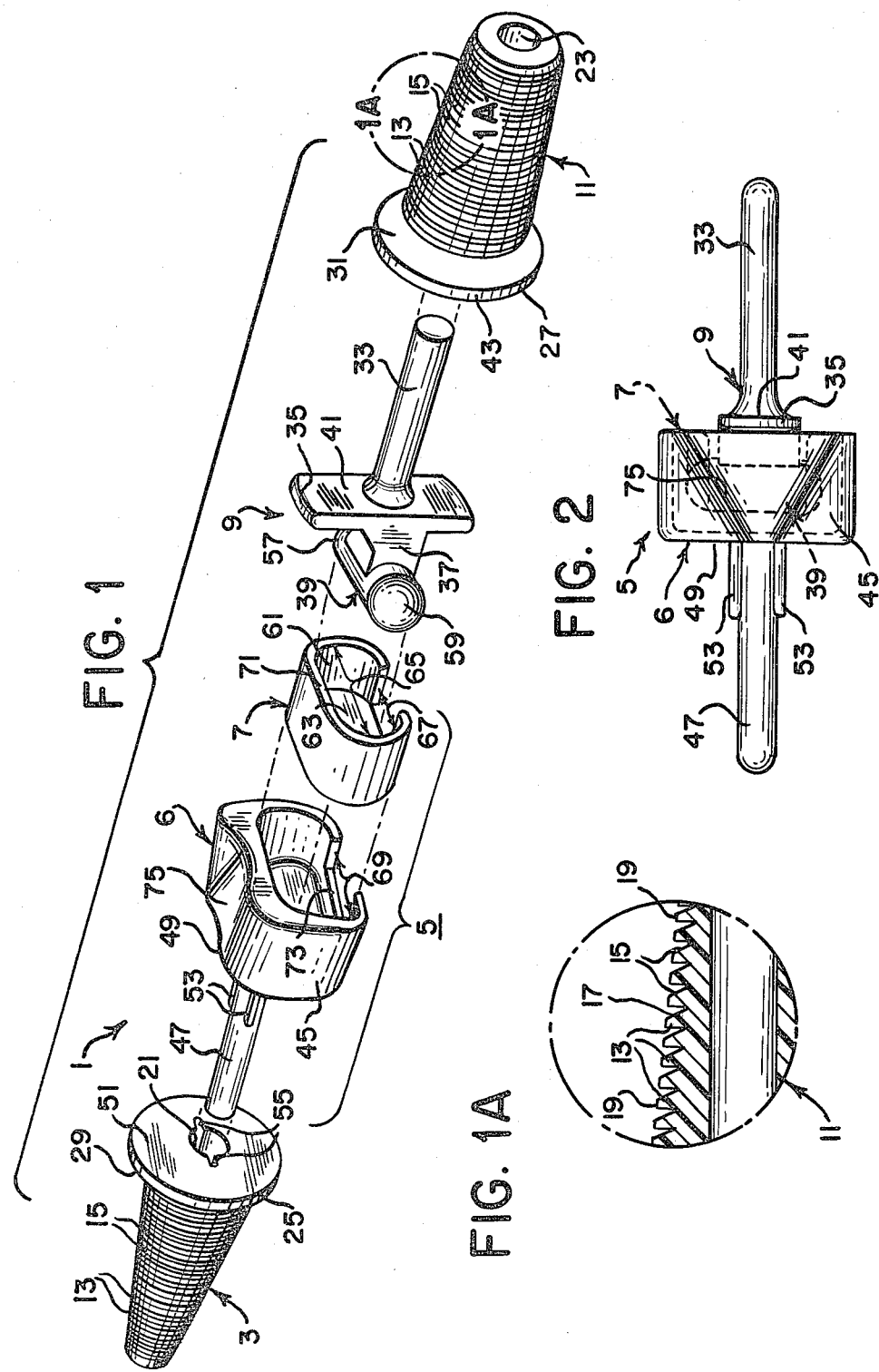

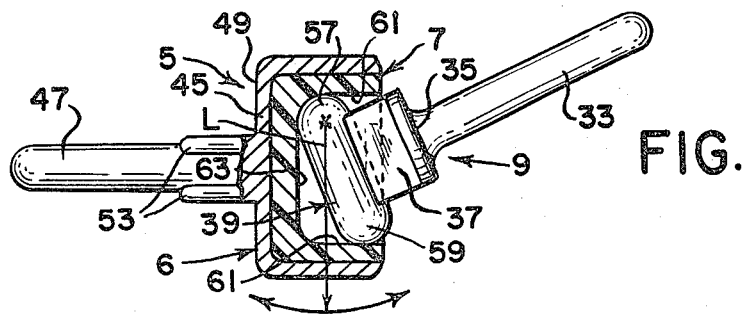
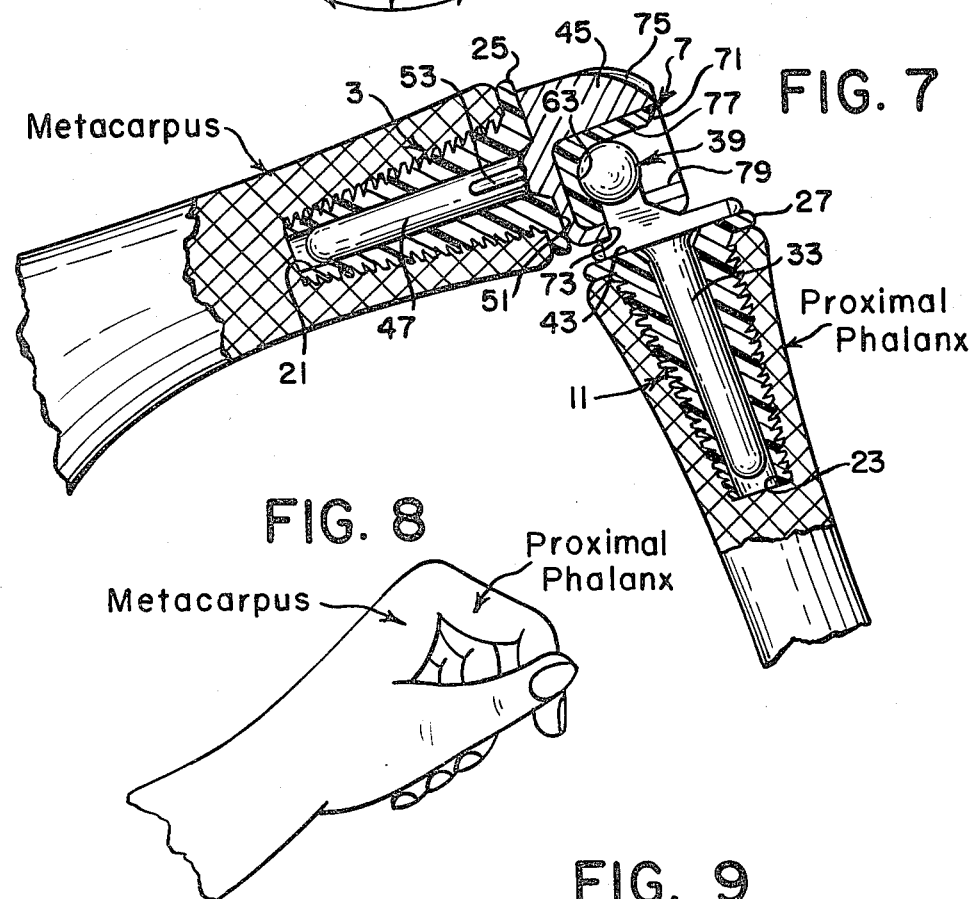
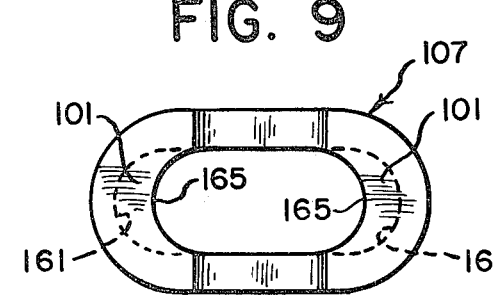

JOINT PROSTHESIS

This is a continuation of application Ser. No. 017,486, filed Mar. 5, 1979, now abandoned.

BACKGROUND OF THE INVENTION

This invention relates to joint prostheses, in particular finger joint prostheses and most particularly prostheses for the metacarpophalangeal joint. A variety of prostheses for use in the surgical repair of diseased or damaged finger joints are known. One type of prior art device (see, e.g., U.S. Pat. Nos. 3,462,765 and 3,593,342) consists of a unitary flexible rubber body having stems for fixation within the intramedullary canals of the two bones forming the joint. Although widely used, this type of prosthesis has certain disadvantages. For example, rubber with adequate flexibility has less than the desired level of mechanical strength, and some mechanical degradation and even breakage of this type of prosthesis under the conditions of actual use have been observed clinically. Also, these prostheses can have a highly unnatural feel in the body because they do not always flex at the desired point or adequately control radio-ulnar rotations, and because they provide an insufficient moment arm to the extensor tendon to overcome extensor lag.

A second type of prior art finger joint prosthesis (see, e.g., U.S. Pat. Nos. 3,506,982; 4,011,603 and 4,059,854) comprises two components, with the metal protuberant head portion of one component snapping into and retained by the plastic housing of the other component. This type of prosthesis generally provides a more accurate reproduction of the movement of the natural finger joints than the unitary rubber implants, but nevertheless is basically a linked device and thus can feel awkward and overly constrained in the body of a patient. The forces inherent in the mechanical constraint of this type of prosthesis are transmitted to the plastic housing, which can fail by creep or fracture.

An always potential problem with the use of joint prostheses generally is the loosening of the fixation between an intramedullary stem of the prosthesis and the wall of the intramedullary canal of the host bone under the influence of the stresses experienced in use at the bone-prosthesis fixation interface. This problem may develop whether the fixation is by cement, bone tissue ingrowth, or alternative method. Torsional, shear, tensile and compressive forces upon the prosthesis are generally transmitted to the bone-prosthesis fixation interfaces, which may then be weakened by the constantly recurring action of these forces.

Therefore, it would be highly beneficial to the art to provide a class of joint prosthesis wherein the transmission of forces acting upon the prosthesis to the bone-prosthesis fixation interfaces is minimized, thus assuring the integrity of the fixation obtained after implantation and, e.g. tissue ingrowth, and also reducing the risk of subsequent loosening of the fixation during use of the prosthesis. Also, in the case of the metacarpophalangeal joint, it would be highly beneficial to provide a new prosthesis reproducing the motion and degrees of freedom of the natural joint, without, of course, sacrificing the mechanical stability of the device.

SUMMARY OF THE INVENTION

A novel prosthesis for a joint of a first bone with a second bone has now been invented, comprising a first component, a second component in articulatory bearing relationship with said first component, said first component being operatively connected to said first bone, said second component being operatively connected to said second bone, and the connection of at least one of said components to its bone being such as to provide for relative longitudinal movement between said component and its bone. Although of particular interest as a finger joint prosthesis, especially a metacarpophalangeal joint prosthesis, the novel prosthesis may also be adapted for use in other joints, e.g. the elbow or the knee.

Of particular interest is a novel prosthesis for a joint of a first bone with a second bone comprising a first intramedullary plug adapted to be secured to the wall of the intramedullary canal of said first bone and provided with a longitudinal bore therein, a second intramedullary plug adapted to be secured to the wall of the intramedullary canal of said second bone and provided with a longitudinal bore therein, a first component comprising a bearing portion and a stem extending therefrom and a second component comprising a bearing portion and a stem extending therefrom, with said stems of said first and second components being longitudinally slidably received in said bores in said first and second intramedullary plugs, respectively, and with said bearing portions of said first and second components being in mutual articulatory engagement. Because the stems of the first and second components are free to longitudinally slide within the bores receiving them, the transmission of tensile forces exerted upon the prosthesis to the plug-bone fixation interfaces is virtually eliminated. Also, the transmission of compressive forces as shear upon the plug-bone fixation interfaces can be greatly reduced.

The intramedullary plugs are preferably made of plastic with the slidable stems of the two components preferably made of metal or metal alloy, thereby reducing wear and friction between the plugs and stems. The bearing portion of one of said components (the distal component in the case of a metacarpophalangeal joint prosthesis) preferably presents a convex metal or metal alloy bearing surface to the other component, and the bearing portion of said other component preferably includes a removable plastic bearing insert which presents a concave bearing surface to, and contacts in use, said convex bearing surface. Use of such a removable plastic bearing insert will, of course, greatly reduce wear and friction between the bearing portions of the two components.

In a preferred metacarpophalangeal joint prosthesis embodiment, the prosthesis is provided with means to prevent either rotation of the proximal component relative to the proximal intramedullary plug about the longitudinal axis of the metacarpus, or rotation of the distal component relative to the distal intramedullary plug about the longitudinal axis of the proximal phalanx, but not both. As a result of this feature, which can of course be incorporated into prostheses for other joints as well, the transmission of most torsional forces exerted upon the prosthesis to the plug-bone fixation interfaces as shear is also virtually eliminated or substantially reduced, without detracting from the inherent mechanical stability of the prosthesis.

Another aspect of a novel metacarpophalangeal joint prosthesis of the invention concerns the design and interaction of the bearing portions of the two components in the prosthesis, which afford a movement and degrees of freedom similar to those of the natural metacarpophalangeal joint.

DETAILED DESCRIPTION OF THE INVENTION

The invention will be described in detail with reference to a preferred embodiment thereof, which is a metacarpophalangeal joint prosthesis. Reference to this embodiment does not limit the scope of the invention, which is limited only by the scope of the claims.

In the drawings:

FIG. 1 is an exploded perspective view of a metacarpophalangeal joint prosthesis of the invention;

FIG. 1A is an enlarged view of a portion of the phalangeal intramedullary plug of the prosthesis of FIG. 1 showing the bone tissue ingrowth surface in greater detail;

FIG. 2 is a top plan view of the components of the prosthesis of FIG. 1 in mutual engagement at extension;

Figure 3:
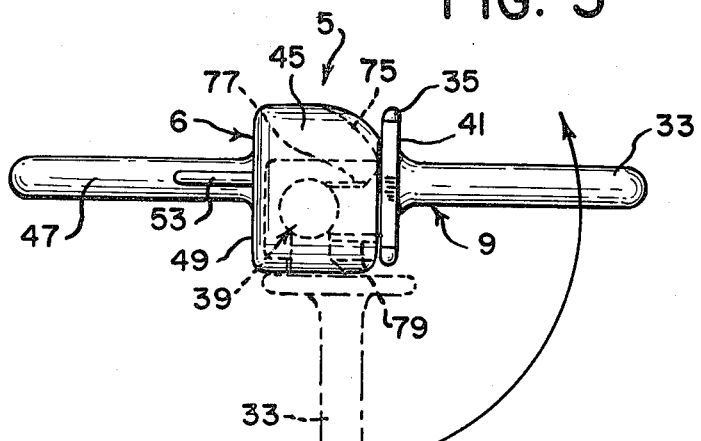
FIG. 3 is a side elevation of the components of the prosthesis of FIG. 1 in mutual engagement at extension, with the components at flexion (phantom outline) and the direction of articulation of the prosthesis shown.
Figure 4:
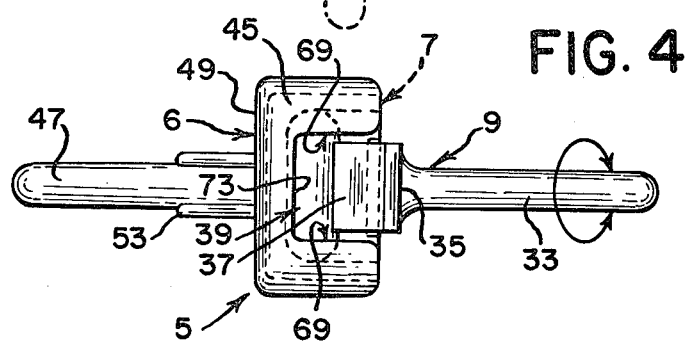
FIG. 4 is a bottom plan view of the components of the prostheses of FIG. 1 in mutual engagement at extension, with the axial rotation of the stem of the phalangeal component within the longitudinal bore in the phalangeal intramedullary plug shown.
Figure 5:
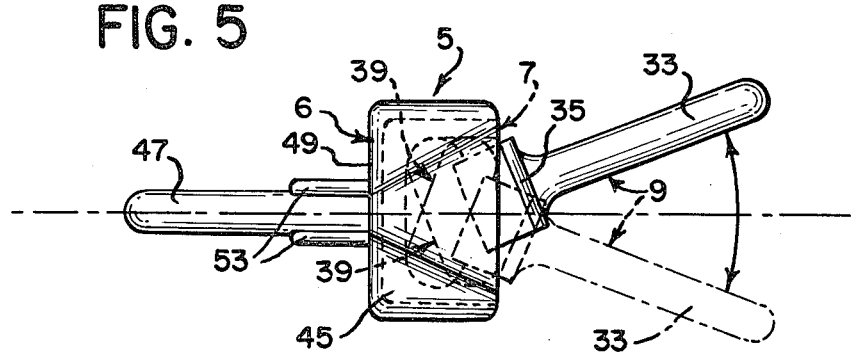
FIG. 5 is a view similar to FIG. 2, illustrating radioulnar rocking of the phalangeal component with respect to the metacarpal component at extension.

FIG. 6 is a bottom view of the components of the prosthesis of FIG. 1 in mutual engagement at extension with the phalangeal component substantially rotated with respect to the metacarpal component via radioulnar rocking, in which the volar half of the socket portion of the metacarpal component is cut-away and the moment arm available to the collateral ligament for restoration of the prosthesis shown;

FIG. 7 is a side elevation of the prosthesis of FIG. 1 secured within the intramedullary canals of the metacarpus and proximal phalanx at nearly full flexion, with parts of the intramedullary plugs cut-away;

FIG. 8 is a perspective view of a left human hand with the thumb pressing against the tip of the index finger in a type of pinching action against which the prosthesis of FIG. 1 is resistant; and FIG. 9 is a frontal view of a modified version of the plastic bearing insert of the metacarpal component of the prosthesis of FIG. 1.

A preferred embodiment of the invention, i.e. a metacarpophalangeal joint prosthesis 1, is shown in FIGS. 1 to 7. Prosthesis 1 consists of a plastic metacarpal intramedullary plug 3, a metacarpal component 5 consisting of a metal housing member 6 and a plastic bearing insert 7, a metal phalangeal component 9 and a plastic phalangeal intramedullary plug 11. The metacarpus and proximal phalanx of the surgically repaired metacarpophalangeal joint are shown in FIG. 7. The various ligaments and tendons participating in the natural joint, e.g. the collateral ligaments, are not shown in FIG. 7 but will generally be viable and remain in place.

Intramedullary plugs 3 and 11 are preferably made of ultra high molecular weight polyethylene. They can be provided in various different sizes so that their dimensions can be matched to the size of the bones of the recipient. Metacarpal plug 3 is generally larger than phalangeal plug 11. Both plugs are tapered with decreasing cross-sectional area towards the extremities of the prosthesis. Prior to insertion of an intramedullary plug, the intramedullary canal is reamed to a diameter slightly less (by about 0.02 inches) than the diameter of the plug so that the plug can be press-fitted against the wall of the canal. The exteriors of plugs 3 and 11 are provided (see FIG. 1A) with laterally extending ridges, e.g. 13, defining between them laterally extending grooves, e.g. 15. The walls of the ridges facing away from the contact area of the two components, e.g. wall 17, are sloped so as to minimize resistance to insertion of the plugs within the intramedullary canals. Withdrawal of the inserted plugs, however, is rendered very difficult by the biting action of the flat tips, e.g. 19, of the ridges against the walls of the canals. Permanent fixation is obtained by bone tissue ingrowth within the space of the grooves, e.g. 15. Permanent fixation may, of course, be achieved by other known methods, such as by the use of an orthopedic cement.

Each of intramedullary plugs 3 and 11 is provided with a longitudinal bore 21 and 23 aligned along the central axis of the plug and open to both ends of the plug. Each of plugs 3 and 11 terminates at its end facing toward the contact area of the two components with a circular flange 25 and 27, the back faces 29 and 31 of which seat respectively against the resected extremities of the metacarpus and the proximal phalanx. As can be seen from FIG. 7, only minimal resection of natural bone is required for the surgical insertion of intramedullary plugs 3 and 11.

Phalangeal component 9 may be a unitary cast surgical implant alloy article. A highly suitable alloy is Vitallium ® (Howmedica Inc.; New York, N.Y.). Component 9 consists of a stem 33, a flange 35 at the proximal end of stem 33, a neck portion 37 extending from the proximal face of flange 35 and a protuberant head portion 39, also referred to herein as the bearing portion, carried by neck portion 37. Stem 33 is slidably and rotatably received within longitudinal bore 23 in the phalangeal intramedullary plug 11. A limit on the extent of insertion is reached when the distal face 41 of flange 35 seats against the front face 43 of flange 27 on plug 11. Flange 35 is shaped as a circle with two equal and opposed lateral segments removed (see FIG. 1) so as not to prevent substantial radio-ulnar rocking at extension.

Metacarpal component 5 consists of metal housing member 6 and plastic bearing insert 7. Housing member 6 may be a unitary cast surgical implant alloy article, preferably of Vitallium ® (Howmedica Inc.; New York, N.Y.). Housing member 6 consists of female head portion 45 and stem 47 extending therefrom in the proximal direction. Head portion 45 and plastic bearing insert 7 taken together comprise the bearing portion, also referred to herein as the socket portion, of the metacarpal component 5. Removable plastic bearing insert 7 is retained within head portion 45 by frictional fit. In the unusual event that substantial wear occurs in an insert 7 during use of the prosthesis, the insert may be removed surgically and replaced with a new one, with minimal disruption of the remainder of the surgically repaired metacarpophalangeal joint. Insert 7 is preferably made of ultra high molecular weight polyethylene.

Stem 47 is slidably received within longitudinal bore 21 in the metacarpal intramedullary plug 3. A limit on the extent of insertion is reached when the rear face 49 of head portion 45 seats against the front face 51 of flange 25 on plug 3. One or more longitudinal fins (a pair of such fins, e.g. 53, are shown in the drawings)

projecting from the exterior of stem 47 are received within corresponding longitudinal slots, e.g. 55, in the wall of bore 21, thereby preventing rotation of component 5 relative to intramedullary plug 3 about the longitudinal axis of the metacarpus.

Since axial rotation of *only one* of the two components of prosthesis 1 with respect to the plug receiving it is allowed, the situation can never arise wherein *both* components 5 and 9 rotate with respect to the two bones forming the joint while remaining fixed relative to each other.

Means to prevent rotation of metacarpal component 5 with respect to plug 3 about the longitudinal axis of the metacarpus other than those shown in the drawings may be employed. Thus, for example, front face 51 of flange 25 may have a concave cylindrical surface which interacts with a totally or partially conforming convex cylindrical surface of rear face 49 of head portion 45 so as to stabilize plug 3 and component 5 against relative rotation. Use of this alternate means to prevent rotation eliminates the need for the fins, e.g. 53, and slots, e.g. 55, shown in the drawings.

As a result of the configurations of plugs, stems and flanges illustrated in the drawings, the transmission of forces exerted upon the prosthesis to the bone-plug fixation interfaces is greatly reduced. The transmission of tensile stresses to the fixation interfaces is eliminated because stems 47 and 33 are free to slide longitudinally within bores 21 and 23 in plugs 3 and 11. Compressive stresses are transmitted by head portion 45 and flange 35 to plug flanges 25 and 27, and then distributed primarily as compression upon the resected cortical rims against which the plug flanges are seated and along the substantial surface area of the tapered walls of the intramedullary canals. Thus, transmission of compressive stresses as shear upon the fixation interfaces is effectively minimized. The transmission of torsional stresses of a kind creating a torsional moment about the longitudinal axis of the proximal phalanx is also virtually eliminated because of the freedom of stem 33 to rotate within bore 23 in plug 11. The proportion of torsional stresses of a kind creating a torsional moment about the longitudinal axis of the metacarpus that is transmitted as shear upon the metacarpal bone-plug fixation interface is given approximately by the sine of the angle of flexion (or hyper-extension). Shear forces acting upon components 5 and 9 of prosthesis 1 do exert small bending moments upon plugs 3 and 11 which are distributed along the lengths of said plugs. The stresses along the fixation interfaces resulting from these small bending moments are more evenly distributed because of the softness of the plastic plugs and have little effect on fixation integrity. Thus, in conclusion, the risk of motion of the plugs with respect to the walls of the intramedullary canals during the tissue ingrowth period and the risk of loosening of the fixations during the subsequent use of the prosthesis are both generally reduced.

Head portion 39 of phalangeal component 9 is cylindrical with rounded ends 57 and 59. Preferably, ends 57 and 59 are hemispheroidal as shown in the drawings. The longitudinal axis of cylindrical head portion 39 is perpendicular to the plane of articulation of the prosthesis (see FIG. 3). The inner walls of plastic bearing insert 7 define a socket cavity 61 by which cylindrical head portion 39 is slidably received when components 5 and 9 are mutually engaged. The concave proximal inner wall 63 of plastic bearing insert 7 serves as the bearing surface of metacarpal component 5. Surface 63 is half cylindrical in shape with rounded ends and comforms closely in shape with cylindrical head portion 39, so that bearing surface 63 and head portion 39 fit together snugly when the prosthesis 1 is under compression. Socket cavity 61 extends distally from bearing surface 63 to aperture 65 in the distal end of insert 7. Aperture 65 has approximately the same dimensions as a cross-section taken through the longitudinal axis of head portion 39. Therefore, head portion 39 can freely slide through aperture 65 to enter socket cavity 61. A slot 67 in the volar wall of insert 7 extends distally from bearing surface 63 until it communicates with aperture 65. As prosthesis 1 is flexed (see FIG. 3), neck portion 37 of phalangeal component 9 passes through volar slot 67 in insert 7 and a registered slot 69 in head portion 45. Sufficient clearance is provided so that neck portion 37 does not contact the side walls defining either of slots 67 and 69. Articulation is limited by abutment of neck portion 37 of phalangeal component 9 against surface 71 of plastic bearing insert 7 and surface 73 of metal housing member 6. A range of articulation of from about 20° of hyper-extension to about 90° of flexion is permitted.

Prosthesis 1 accurately reproduces the ranges of movement and degrees of freedom of the natural metacarpophalangeal joint, and thus will have a natural and realistic feel when implanted within the body of a patient. Since head portion 39 can slide within socket cavity 61, components 5 and 9 of prosthesis 1 are considerably less constrained and possess greater freedom for relative play than the components of the linked prostheses of the prior art. The freedom of movement of head portion 39 within socket cavity 61 provides an additional means of preventing the transmission of tensile stresses exerted upon the prosthesis to the bone-plug fixation interfaces. The mechanical stability of prosthesis 1 is assisted by the self-stabilizing actions of the various natural ligaments and tendons, e.g. the collateral ligaments and the extensor and flexor tendons. The extensor tendon is retained during flexion in track 75 in the dorsal face of head portion 45. Track 75 has a disto-volar curve. As is shown in FIG. 3, the axis of articulation of prosthesis 1, i.e. the longitudinal axis of head portion 39, is offset volarly from the line defined by the longitudinal axes of stems 33 and 47 at extension, in order to increase the moment arm available to the weaker extensor tendon while still providing an adequate moment arm to the stronger flexor tendon.

The natural metacarpophalangeal joint possesses substantial freedom at extension for relative lateral rocking of the proximal phalanx with respect to the metacarpus, but is highly resistant at flexion to the type of relative rocking movement wherein the proximal phalanx would be rotated about the longitudinal axis of the metacarpus. Thus, for example, the natural flexed metacarpophalangeal joint is highly stable against the type of pinching action illustrated in FIG. 8. Prosthesis 1 reproduces both of these qualities of the natural metacarpophalangeal joint. At extension (see FIGS. 5 and 6), component 9 is mechanically free to laterally rock to a substantial extent (about 25° to either side of the center line) with respect to component 5. A mechanical restraint upon rocking at extension is finally reached by the impingement of component 9 against insert 7. However, the natural collateral ligaments will stabilize the joint prosthesis by themselves in normal use. Note that a 25° lateral rocking displacement at extension of the proximal phalanx with respect to the metacarpus requires an extremely large distention (about 4 to 5 mm.)

of the collateral ligament opposing such displacement. Also, the configurations of head portion 39 and bearing surface 63 of the two components impart a maximum possible moment arm (given anatomical dimensions) to the collateral ligament or intrinsic muscles acting to restore the prosthesis. The moment arm available for such restoration is shown approximately as length L drawn from the center of rotation of the prosthesis in FIG. 6. The forces exerted upon component 9 by the collateral ligaments in bringing about radio-ulnar rocking at extension and restoring the prosthesis from such rocking are transmitted as compressive stresses to component 5 and then to flange 25, without exerting shear forces on component 5 and thus without placing bending moments upon stems 33 and 47.

At flexion, forces upon the prosthesis which would tend to cause rotation of component 9 about the longitudinal axis of the metacarpus (see, e.g., FIG. 8) are resisted by the contact of head portion 39 against the dorsal and volar walls 77 and 79 of plastic bearing insert 7 and the cooperation of fins, e.g. 53, with slots, e.g. 55. Additionally, as already indicated, torsional stresses upon the prosthesis of a kind tending to rotate cylindrical head portion 39 about the longitudinal axis of the proximal phalanx are in fact ineffective to cause such rotation because of the freedom of stem 33 to rotate within longitudinal bore 23 in intramedullary plug 11.

In a modification of metacarpal component 5 shown in FIG. 9 and within the scope of the present invention, lips 101 are provided at the distal end of plastic bearing insert 107 to reduce the size of aperture 165. The purpose of lips 101 is to prevent dislocations resulting from extreme relative displacement of the components under tension or extreme relative radio-ulnar rocking of the components (greater than about 30° to either side of center). Head portion 39 is engaged within socket cavity 161 by pressure fit. Relative radio-ulnar rocking at extension and relative component separation longitudinally of the metacarpal component are *mechanically unrestrained in normal use,* i.e., controlled and limited under non-extreme conditions only by natural anatomical means, e.g. ligaments and tendons. Since lips 101 would only be contacted in use by head portion 39 in an unusual extreme situation, head portion 39 is not retained or embraced firmly by said lips within the socket cavity in the same manner as are the head portions of the embodiments described in U.S. Pat. Nos. 3,506,982; 4,011,603 and 4,059,854.

It is to be understood that the aspect of the invention described herein relating to the detailed configurations of metacarpophalangeal joint prosthesis bearing portions may be practiced without employing the other aspect of the invention involving motion of component stems within intramedullary plugs. Thus, for example, the metacarpophalangeal joint prosthesis component stems may be secured directly to the walls of the intramedullary canals by tissue ingrowth, cement, or other fixation means. Likewise, said other aspect of the invention relating to the motion of component stems within intramedullary plugs may be practiced while employing bearing portion designs, such as those described in U.S. Pat. Nos. 3,506,982; 4,011,603 and 4,059,854, distinct from those described herein. As was stated earlier, said other aspect of the invention is not restricted to metacarpophalangeal joint prostheses, but has general applicability to other types of joint prostheses as well. It is preferred, however, to employ both aspects of the invention together to obtain the optimum metacarpophalangeal joint prosthesis.

What is claimed is:

1. A finger joint prosthesis for a finger joint of a first bone with a second bone comprising a first component, a second component in articulatory bearing relationship with said first component, said first component capable of being operatively connected to said first bone, and said second component capable of being operatively connected to said second bone, wherein the connections of said first and second components to said first and second bones, respectively, is such as to provide in normal use for mechanically unrestrained relative movement between each of said components and its bone longitudinally of said bone.

2. The finger joint prosthesis of claim 1 wherein said finger joint is the metacarpophalangeal joint.

3. The finger joint prosthesis of claim 2 wherein said first bone is the proximal phalanx.

4. A finger joint prosthesis for a finger joint of a first bone with a second bone comprising a first component, a second component in articulatory bearing relationship with said first component, said first component capable of being operatively connected to said first bone, said second component capable of being operatively connected to said second bone, and the connection of said first component to said first bone being such as to provide for relative rotation between said first component and said first bone about the longitudinal axis of said first bone, wherein the connection of said second component to said second bone is such as to provide in normal use for mechanically unrestrained relative movement between said second component and said second bone longitudinally of said bone.

5. A finger joint prosthesis for a finger joint of a first bone with a second bone comprising a first component, a second component in articulatory bearing relationship with said first component, said first component capable of being operatively connected to said first bone, said second component capable of being operatively connected to said second bone, the connection of said first component to said first bone being such as to provide for relative rotation between said first component and said first bone about the longitudinal axis of said first bone, and wherein the connections of said first and second components to said first and second bones, respectively, is such as to provide in normal use for mechanically unrestrained relative movement between each of said components and its bone longitudinally of said bone.

6. The finger joint of claim 5 wherein the connection of said second component to said second bone is such as to prevent relative rotation between said second component and said second bone about the longitudinal axis of said second bone.

7. A finger joint prosthesis for a metacarpophalangeal joint of a first bone with a second bone comprising a first component, a second component in articulatory bearing relationship with said first component, said first component capable of being operatively connected to said first bone, said second component capable of being operatively connected to said second bone, and the connection of said first component to said first bone being such as to provide for relative rotation between said first component and said first bone about the longitudinal axis of said first bone, and wherein the connections of said first and said second components to said first and said second bones, respectively, is such as to provide in normal use for mechanically unrestrained relative movement between each of said components and its bone longitudinally of said bone.

8. A finger joint prosthesis for a metacarpophalangeal joint of a proximal phalanx with a second bone comprising a first component, a second component in articulatory bearing relationship with said first component, said first component capable of being operatively connected to said proximal phalanx, said second component capable of being operatively connected to said second bone, and the connection of said first component to said proximal phalanx being such as to provide for relative rotation between said first component and said proximal phalanx about the longitudinal axis of said proximal phalanx, and wherein the connections of said first and said second components to said proximal phalanx and said second bone, respectively, is such as to provide in normal use for mechanically unrestrained relative movement between each of said components and its bone longitudinally of said bone.

9. A finger joint prosthesis for a finger joint of a first bone with a second bone comprising:
a first intramedullary plug adapted to be secured to the wall of the intramedullary canal of said first bone and provided with a longitudinal bore therein;
a first component comprising a bearing portion and a stem extending therefrom, with said stem being disposed within said longitudinal bore such as to provide for relative rotation between said stem and said bore about the longitudinal axis of said bore;
a second component comprising a bearing portion and a stem extending therefrom for insertion with the intramedullary canal of said second bone;
with said bearing portions of said first and second components being in mutual articulatory engagement; and
wherein the connection of said second component to said second bone is such as to provide in normal use for mechanically unrestrained relative movement between said second component and said second bone longitudinally of said bone.

10. The finger joint prosthesis of claim 9 wherein said finger joint is the metacarpophalangeal joint.

11. The finger joint prosthesis of claim 10 wherein said first bone is the proximal phalanx.

12. An articulating metacarpophalangeal joint prosthesis comprising:
a first component comprising a stem for insertion within the intramedullary canal of a first bone, a neck portion at one end of said stem and a protuberant head portion on said neck portion,
said head portion being of generally cylindrical shape with rounded ends and with the longitudinal axis of said head portion being perpendicular to the plane of articulation of said prosthesis; and
a second component comprising a stem for insertion within the intramedullary canal of a second bone and a socket portion at one end of said stem including inside walls for defining a socket cavity bounded at one end by a concave bearing surface with which said head portion is capable of snugly fitting, said socket portion being dimensioned and configured such that the dimension of the socket cavity along the longitudinal axis of the second component is greater than the diameter of the head portion along the longitudinal axis of the first component,
said socket portion including an aperture in the end thereof facing away from said second bone, said inside walls including a volar and a dorsal wall, said volar wall having a longitudinal slot,
means for mechanically restraining said second component from rotating about the longitudinal axis of said second bone,
said inside walls of said socket cavity extending axially of said second component from said bearing surface to the peripheral edge of said aperture such that said socket cavity communicates with said longitudinal slot of said volar wall and said aperture,
said head portion of said first component capable of being received by and slidingly movable within said socket cavity generally along the longitudinal axis of the second component, with said neck portion of said first component capable of being located in said slot in said volar wall of said socket portion as said joint prosthesis is flexed,
the configuration of said socket cavity being such so as to permit in normal use mechanically unrestrained relative radio-ulnar rocking of said two components when said joint prosthesis is substantially extended and also to permit mechanically unrestrained relative separation of said head portion and said concave bearing portion longitudinally of said second component.

13. The finger joint prosthesis of claim 12 wherein said socket portion is dimensioned and configured such that said head portion is contiguous to the dorsal and volar walls of said socket portion so as to prevent rotation of said head portion relative to said socket portion about the longitudinal axis of said second bone.

14. The finger joint prosthesis of claim 12 wherein said first bone is the proximal phalanx and said second bone is the metacarpus.

15. The finger joint prosthesis of claim 14 wherein said prosthesis includes a first intramedullary plug adapted to be secured to the wall of the intramedullary canal of the proximal phalanx and provided with a longitudinal bore therein, with said stem portion of said first component being rotatably received within said longitudinal bore.

16. The finger joint prosthesis of claim 12 wherein said head portion of said first component is made of metal or metal alloy and said socket cavity is defined by the walls of a removable plastic bearing insert contained within said socket portion of said second component.

17. The finger joint prosthesis of claim 16 wherein said first bone is the proximal phalanx and said second bone is the metacarpus.

18. The finger joint prosthesis of claim 16 wherein said plastic bearing insert is provided with lip means at the end of said insert facing away from said second bone, with said lip means reducing the size of said aperture so as to prevent dislocation of said prosthesis as a result of abnormal relative radio-ulnar rocking of said two components or abnormal relative separation of said two components longitudinally of said second component.

19. The finger joint prosthesis of claim 12 wherein said head portion of said first component is capable of freely sliding through said aperture to enter said socket cavity.

20. An articulating metacarpophalangeal joint prosthesis wherein the first bone is the proximal phalanx and the second bone is the metacarpus comprising:

a first component comprising a stem for insertion within the intramedullary canal of a first bone, a neck portion at one end of said stem and a protuberant head portion on said neck portion, with said head portion being of generally cylindrical shape with rounded ends and with the longitudinal axis of said head portion being perpendicular to the plane of articulation of said prosthesis; and a second component comprising a stem for insertion within the intramedullary canal of a second bone and a socket portion at one end of said stem having walls defining a socket cavity bounded at one end by a concave bearing surface with which said head portion is capable of snugly fitting, the dimension of the socket cavity along the longitudinal axis of the second component being greater than the diameter of the head portion, with said socket cavity extending longitudinally from said bearing surface to an aperture in the end of said socket portion facing away from said second bone, with the volar wall of said socket portion being provided with a longitudinal slot communicating with said socket cavity and said aperture, with said head portion of said first component being received by and slidingly movable within said socket cavity generally along the longitudinal axis of the second component, with said neck portion of said first component being located in said slot in said volar wall of said socket portion as said joint prosthesis is flexed, and with said second component being mechanically restrained from rotating about the longitudinal axis of said second bone, whereby the shape of said socket cavity is such as to permit in normal use mechanically unrestrained relative radio-ulnar rocking of said two components when said joint prosthesis is substantially extended and mechanically unrestrained relative separation of said two components longitudinally of said second component, and is also such as to prevent, by the contact of said head portion against the dorsal and volar walls of said socket portion, rotation of said head portion of said first component relative to said socket portion of said second component about the longitudinal axis of said second bone, wherein said prosthesis includes a first intramedullary plug adapted to be secured to the wall of the intramedullary canal of the proximal phalanx and provided with a longitudinal bore therein, with said stem portion of said first component being rotatably received within said longitudinal bore, and wherein said prosthesis includes a second intramedullary plug adapted to be secured to the wall of the intramedullary canal of the metacarpus and provided with a longitudinal bore therein, with said stem portions of said first and second components both being longitudinally slidably received in said bores in said first and second intramedullary plugs, respectively.

21. A finger joint prosthesis comprising:

a proximal intramedullary plug adapted to be secured to the wall of the intramedullary canal of the proximal bone and provided with a longitudinal bore therein;

a distal intramedullary plug adapted to be secured to the wall of the intramedullary canal of the distal bone and provided with a longitudinal bore therein;

a proximal component comprising a bearing portion and a steam extending therefrom; and a distal component comprising a bearing portion and a stem extending therefrom, with said stems of said proximal and distal components being in normal use received for mechanically unrestrained longitudinal sliding movement in said bores in said proximal and distal intramedullary plugs, respectively, and with said bearing portions of said proximal and distal components being in mutual articulatory engagement.

22. The finger joint prosthesis of claim 21 wherein said finger joint is the metacarpophalangeal joint, said proximal bone is the metacarpus and said distal bone is the proximal phalanx.

23. The finger joint prosthesis of claim 22 wherein said prosthesis contains means to prevent rotation of at least one of said components relative to the intramedullary plug receiving it about the longitudinal axis of the bone to which said plug is secured.

24. The finger joint prosthesis of claim 23 wherein rotation of only one of said components relative to the intramedullary plug receiving it about the longitudinal axis of the bone to which said plug is secured is prevented.

25. The finger joint of claim 24 wherein said rotation preventing means comprises one or more longitudinal fins projecting from the exterior of the stem of the component whose rotation is prevented and corresponding longitudinal slots to receive said fins in the wall of the longitudinal bore in the intramedullary plug with which said component is slidingly engaged.

26. The finger joint prosthesis of any of claims 24 or 25 wherein rotation of said proximal component relative to said proximal intramedullary plug about the longitudinal axis of the metacarpus is prevented.

27. The finger joint prosthesis of any of claims 21 or 22 wherein said proximal and distal intramedullary plugs both terminate, at their distal and proximal ends, respectively, with flanges adapted to seat against the cortical surfaces of said proximal and distal bones, respectively, and to distribute upon said surfaces a substantial portion of compressive forces exerted in use upon said prosthesis.

28. The finger joint prosthesis of claim 27 wherein each of said intramedullary plugs is tapered so as to have decreasing cross-sectional area with increasing distance from the flange-terminated end of said plug.

29. The finger joint prosthesis of claim 21 wherein said intramedullary plugs are made of plastic and said stems of said proximal and distal components are made of metal or metal alloy.

30. The finger joint prosthesis of claim 29 wherein the bearing portion of one of said components presents a convex metal or metal alloy bearing surface to the other component, and the bearing portion of said other component includes a removable plastic bearing insert which presents a concave bearing surface to, and contacts in use, said convex bearing surface.

31. The finger joint prosthesis of claim 30 wherein said finger joint is the metacarpophalangeal joint, said proximal bone is the metacarpus, said distal bone is the proximal phalanx, and said convex bearing surface is presented by the bearing portion of said distal component.

* * * * *